(12) United States Patent
Kaupp et al.

(10) Patent No.: US 10,215,708 B2
(45) Date of Patent: Feb. 26, 2019

(54) INSPECTION APPARATUS AND INSPECTION METHOD FOR INSPECTION OF THE SURFACE APPEARANCE OF A FLAT ITEM THAT REPRESENTS A TEST SPECIMEN

(71) Applicant: EyeC GmbH, Hamburg (DE)

(72) Inventors: Ansgar Kaupp, Wohltorf (DE); Soeren Springmann, Hamburg (DE); Dirk Luetjens, Hamburg (DE)

(73) Assignee: EyeC GmbH, Hamburg (DE)

( * ) Notice: Subject to any disclaimer, the term of this patent is extended or adjusted under 35 U.S.C. 154(b) by 0 days.

(21) Appl. No.: 15/606,113

(22) Filed: May 26, 2017

(65) Prior Publication Data

US 2017/0343482 A1    Nov. 30, 2017

(30) Foreign Application Priority Data

May 27, 2016   (DE) ................. 10 2016 109 803

(51) Int. Cl.
  *G01N 21/95*   (2006.01)
  *G01N 21/88*   (2006.01)
  (Continued)

(52) U.S. Cl.
  CPC ..... *G01N 21/8806* (2013.01); *G01N 21/8901* (2013.01); *G01N 21/95* (2013.01);
  (Continued)

(58) Field of Classification Search
  CPC .............. G01N 21/9501; G01N 21/94; G01N 21/8806; G01N 21/47; G01N 2021/4711;
  (Continued)

(56) References Cited

U.S. PATENT DOCUMENTS

| 4,742,225 A | 5/1988 | Chan |
| 4,801,810 A | 1/1989 | Koso |

(Continued)

FOREIGN PATENT DOCUMENTS

| DE | 10 2005 031 647 A1 | 1/2007 |
| DE | 10 2006 008 259 A1 | 8/2007 |

(Continued)

OTHER PUBLICATIONS

European Search Report dated Feb. 6, 2018 in European Application No. 17171115.3 with English translation of the relevant parts.

*Primary Examiner* — Michael P Stafira
(74) *Attorney, Agent, or Firm* — Collard & Roe, P.C.

(57) ABSTRACT

Reflective or embossed regions are supposed to be illuminated as uniformly as possible over the greatest possible angle range for optical inspection using in one aspect an apparatus for inspection having a passive lighting body spotlighted by a spotlight light source, which body illuminates a test region, as well as at least one optical sensor directed at the test region. The lighting body is configured to be partially transmissible, and the optical sensor is disposed, with reference to the test region, optically beyond the lighting body, detecting the test region through the lighting body, and/or the spotlight light source is directed at the lighting body and the lighting body extends continuously over at least 120° in a section plane that stands perpendicular to the surface of the flat items to be tested or inspected.

26 Claims, 4 Drawing Sheets

(51) Int. Cl.
  *G01N 21/89* (2006.01)
  *G01N 21/84* (2006.01)
  *G01N 21/86* (2006.01)
  *G01N 21/896* (2006.01)
(52) U.S. Cl.
  CPC .............. *G01N 2021/845* (2013.01); *G01N 2021/8627* (2013.01); *G01N 2021/8663* (2013.01); *G01N 2021/8812* (2013.01); *G01N 2021/8816* (2013.01); *G01N 2021/8825* (2013.01); *G01N 2021/8962* (2013.01); *G01N 2201/0631* (2013.01); *G01N 2201/0634* (2013.01); *G01N 2201/06153* (2013.01)
(58) Field of Classification Search
  CPC ..... G01N 21/95607; G01N 2021/8822; G01N 2021/8861; G01N 21/956; G01N 21/95623; G01N 15/1434; G01N 15/1459; G01N 2021/8874
  See application file for complete search history.

(56) References Cited

U.S. PATENT DOCUMENTS

| | | |
|---|---|---|
| 5,051,872 A | 9/1991 | Anderson |
| 7,012,241 B2 | 3/2006 | Schnitzlein et al. |
| 7,538,868 B2 * | 5/2009 | Shen .................... G03F 9/7011 356/243.1 |
| 7,602,483 B2 | 10/2009 | Allweier |
| 7,738,089 B2 * | 6/2010 | Lange ................ G01N 21/8806 356/237.1 |
| 8,472,111 B2 * | 6/2013 | Gelernt .................. G02B 21/16 356/51 |
| 8,736,831 B2 * | 5/2014 | Ramachandran .. G01N 21/9501 356/237.1 |
| 8,891,079 B2 * | 11/2014 | Zhao .................... G01N 21/9501 356/237.2 |
| 8,982,345 B2 * | 3/2015 | Kawate ................ G01N 21/474 356/236 |
| 2009/0237653 A1 | 9/2009 | Schnitzlein et al. |

FOREIGN PATENT DOCUMENTS

| | | |
|---|---|---|
| DE | 10 2006 009 593 B4 | 12/2008 |
| DE | 10 2006 017 912 B4 | 4/2009 |
| DE | 10 2008 022 292 B4 | 7/2014 |
| EP | 2 592 328 A1 | 5/2013 |
| JP | 2004-319466 A | 11/2004 |
| JP | 2005-188929 A | 7/2005 |
| JP | 57-55144 B2 | 7/2015 |
| WO | 88/02970 A1 | 4/1988 |
| WO | 02/067567 A1 | 8/2002 |

* cited by examiner

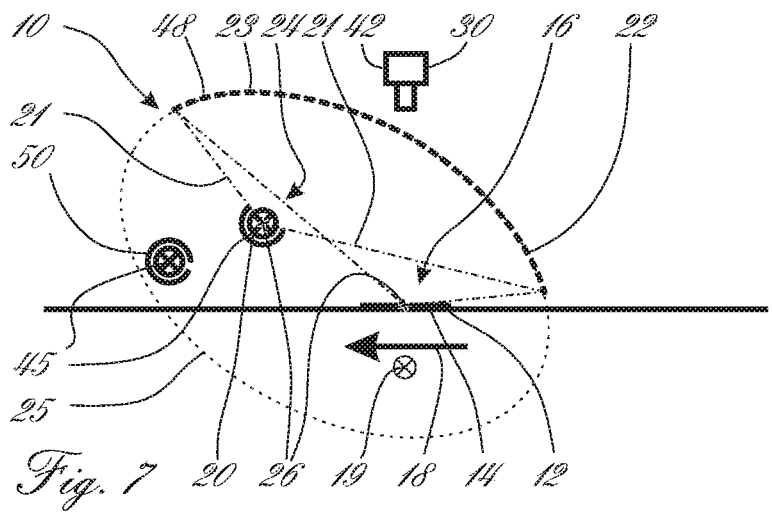
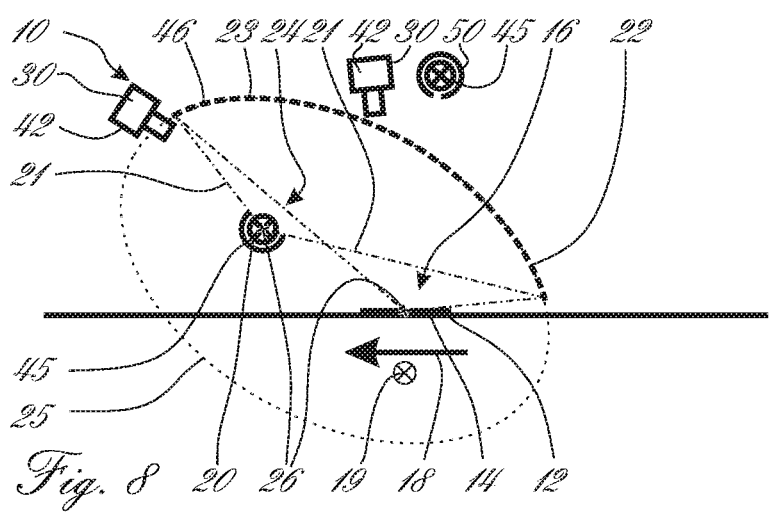
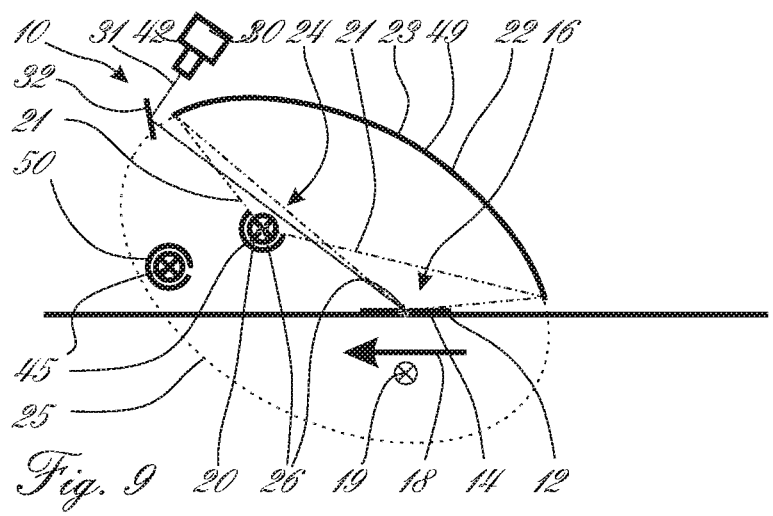

INSPECTION APPARATUS AND INSPECTION METHOD FOR INSPECTION OF THE SURFACE APPEARANCE OF A FLAT ITEM THAT REPRESENTS A TEST SPECIMEN

CROSS REFERENCE TO RELATED APPLICATIONS

Applicant claims priority under 35 U.S.C. § 119 of German Application No. 10 2016 109 803.5 filed May 27, 2016, the disclosure of which is incorporated by reference.

BACKGROUND OF THE INVENTION

1. Field of the Invention

The invention relates to an apparatus for inspection of the surface appearance of a flat item that represents a test specimen. The inspection apparatus comprises a passive lighting body illuminated by a spotlight light source, which body illuminates a test region, or at least one direct light source directed at a test region, as well as at least one optical sensor directed at the test region. Also, the invention relates to a method for inspection of the surface appearance of a flat item representing a test specimen, wherein a test region is indirectly illuminated by way of a passive lighting body illuminated by a spotlight light source, and light proceeding from the test region is detected by way of at least one optical sensor.

2. Description of the Related Art

Such inspection apparatuses and inspection methods and lighting apparatuses or lighting methods that can be used for them are known, for example, from DE 10 2008 022 292 A1, from DE 10 2006 017 912 A1, from DE 10 2006 008 259 A2, from DE 10 2006 009 593 A1, from DE 10 2005 031 647 A1, from JP 57-55144 B2, from JP 2005-188929 A, from WO 88/02970 A1, from U.S. Pat. No. 4,801,810 or from WO 2002/067567 A1. In this regard, with the exception of DE 10 2008 022 292 A1, which serves for examination of essentially three-dimensional structures, all of these lighting apparatuses and lighting methods serve for inspection of flat items, particularly of printed materials, circuit boards, and the like.

SUMMARY OF THE INVENTION

It is the task of the invention to allow inspection of reflective or embossed regions on flat items.

These and other tasks are accomplished by an inspection apparatus and an inspection method having the characteristics of the invention. Further advantageous embodiments, if applicable also independent of these characteristics, are found below.

In this regard, the invention proceeds from the fundamental recognition that reflective or embossed regions should be inspected by means of light that falls onto the test specimen from as many angles as possible.

Thus, an inspection apparatus for inspection of the surface structure of a flat item that represents a test specimen, which apparatus comprises a passive lighting body illuminated by a spotlight light source, which body illuminates a test region, as well as at least one optical sensor directed at the test region, allows inspection of reflective or embossed regions on the flat item, if the inspection apparatus is characterized in that the lighting body is configured to be partially transmissible optically, and the optical sensor is disposed optically beyond the lighting body, with reference to the test region, detecting the test region through the lighting body.

Likewise, an inspection method for inspection of the surface appearance of a flat item that represents a test specimen, wherein a test region is indirectly illuminated by way of a passive lighting body illuminated by a spotlight light source, and light that proceeds from the test region is detected by way of at least one optical sensor, allows inspection of reflective or embossed regions on the flat item if the inspection method is characterized in that the optical sensor detects the test region through the lighting body.

Both the inspection apparatus and the inspection method allow extremely homogeneous illumination of the test specimen, particularly also, in deviation from the state of the art, from the direction of the sensor, which region is considered to be the region of greatest interest, as such. In this manner, the fundamental recognition can also be implemented, that light should fall on the test specimen from the greatest possible number of angles.

In this regard, it should be emphasized that the beam path between the test region and the optical sensor is disrupted by the lighting body, so that illumination by the lighting body also from the direction of the sensor can be guaranteed in the first place. This disruption, brought about by the partial transmissibility of the lighting body, which makes it possible, on the one hand, on the basis of the partial transmissibility, that the optical sensor sees the test region through the lighting body, and, on the other hand, the lighting body reflects or scatters light in the direction of the test region precisely from the direction of the sensor, is not found in the state of the art, in which openings that release the beam path to the respective sensor are provided in the lighting bodies there, so that although the sensor can detect the test region without disruption, specifically no light can be emitted in the direction of the test region or test specimen from the direction of the sensor. Although the simple openings from the state of the art, which release the beam path to the respective sensor, describe a simple, cohesive area in the beam path, the partial transmissibility can be provided by openings that represent multiple non-cohesive areas in the beam path between the test region and the optical sensor in the mathematical sense, wherein accordingly, the lighting body then represents a multi-cohesive area within the beam path, complementary to this.

Also, an inspection apparatus for inspection of the surface appearance of a flat item that represents a test specimen includes a passive lighting body illuminated by a spotlight light source. The body illuminates a test region. At least one optical sensor is directed at the test region. The inspection apparatus allows inspection of reflective or embossed regions of the flat item, if the spotlight light source is directed at the lighting body, and the lighting body extends continuously over at least 120°. Likewise, an inspection method for inspection of the surface appearance of a flat item that represents a test specimen, wherein a test region is indirectly illuminated by way of a passive lighting body illuminated by a spotlight light source, and light proceeding from the test region is detected by way of at least one optical sensor, allows inspection reflective or embossed regions on flat items, if the test region is continuously illuminated over at least 120°. In this regard, continuity of the expanse of the lighting body or the continuity of the illumination allows the most uniform possible lighting of the test region and of a test specimen located there, and this uniformity in turn implements the corresponding fundamental recognition that light falling onto the test specimen from as many angles as possible should be used.

Preferably, the continuous illumination takes place not just over at least 120°, but rather over at least 130° or even over at least 135°, which surprisingly leads to significantly better results.

The angle information above and also listed below holds true in a section plane perpendicular to the surface of the flat items to be tested or inspected. Depending on the concrete requirements, this section plane can particularly have or contain the optical sensor and its beam path. Also, it is conceivable to lay the section plane parallel to a machine direction of the inspection apparatus or perpendicular to a longitudinal expanse direction of the inspection apparatus, as will still be explained in greater detail below, in order to be able to take the corresponding symmetries, as they can be found in the inspection apparatus, into account in this manner.

The uniformity of the light directed at the test specimen, on the basis of the inspection method or inspection apparatuses, makes possible, on the one hand, to avoid excessively high brightness peaks, which could be caused by direct reflection of light into the optical sensor, or to reduce them to a minimum, so that the corresponding appearance can be checked in spite of the presence of possible glossy regions. Likewise, the correspondingly uniform lighting has the result that possible structures, as they are provided, in particular, by means of embossing methods, are minimized in terms of their properties that are disruptive for inspection, because of the uniform lighting. The lighting, which comes from all sides, if possible, makes reflective spheres in the test region appear flat, for example, if the lighting is sufficiently uniform and if focusing of the optical sensor is selected accordingly, so that inspection of the corresponding surfaces can be undertaken.

It is understood that ultimately, the most uniform illumination possible should preferably take place from all sides, so that the corresponding inspection apparatus can preferably be configured with rotation symmetry around the test region, wherein the corresponding axis of rotation then preferably stands perpendicular on the test region, for reasons of symmetry. Because the test region can have a size on the order of approximately 1 mm, particularly a size range between 2.5 mm and 0.5 mm, taking common camera systems into consideration, and taking implementable values for lighting and for common light sources and manageable lighting bodies into consideration, however, corresponding testing of industrially produced flat items, such as, for example, of printed matter, which was printed, embossed or otherwise produced on common printing machines, would be extremely time-consuming and labor-intensive.

For this reason, it is advantageous if the corresponding inspection apparatuses are configured to extend longitudinally, and if a test specimen runs through them along a machine direction, wherein the longitudinal expanse direction is preferably selected to be perpendicular to the machine direction and perpendicular to the surface of the flat items to be tested or inspected, and is also referred to as the transverse direction.

Such an arrangement makes it possible for relatively wider flat items to be subjected to inspection on an industrial scale, quickly and in operationally reliable manner, wherein it has been shown that lighting in a plane from the greatest possible number of angles already leads to sufficiently good uniformization of the test region illuminated in this way, even in the presence of reflective or embossed regions on the respective flat item, in order to allow inspection.

In particular, the inspection apparatus can be configured in such a manner that it guarantees continuous lighting of the test region over at least 120°, in particular over at least 130° or even over at least 135°, and this continuous lighting accordingly leads to a uniform appearance.

The lighting body can be a semi-transmissible mirror, for example, or comprise such a mirror, thereby making it easily possible to implement semi-transmissibility. Cumulatively or alternatively, a light-transmissible diffusive or reflective body can be used as a lighting body configured to be partially transmissible, wherein the light transmissibility can be guaranteed by means of holes or slots, for example, or by means of openings or other measures. Reflective bodies, in particular, appear to be particularly suitable for directing as much light as possible onto the test region, by way of the lighting body that is configured to be partially transmissible, because of their great intensity in reflection, which lies approximately one magnitude above the degree of reflection or backscattering of diffusive bodies.

If the optical sensor is focused appropriately, and if the density of the openings in the diffusive or reflective bodies, such as slots or holes, is sufficient, the diffusive or reflective regions of the diffusive or reflective bodies that remain next to the openings influence the camera image or an image detected by the optical sensor only insignificantly, so that the corresponding disadvantages can easily be accepted, because they are more than outweighed by the uniformity of the resulting lighting.

Thus, for example, the optical sensor can be set relatively closely to the lighting body, so that the lighting body itself is so far outside of the focus that its structurally related influences, which disrupt the beam path to the sensor, do not significantly impair the image detected from the test region, or only impair it in the sense of overall damping.

Reflective bodies having corresponding openings appear to be superior, in particular, also to semi-transmissive mirrors with their losses, but of course combinations of these can also be used.

Frequently, the radiation intensity of the spotlight light source will vary over the spotlighted spatial angle. Likewise, different distances of the lighting body from the test region, as well as varying angles of the surface of the lighting body relative to the test region lead to variations in the light intensity with which the test region is irradiated. In order to counter this disadvantage, the degree of reflection of the semi-transmissible mirror or the light transmissibility and/or back-scattering of its diffusive or reflective body can vary over the expanse of the lighting body. In this way, the light intensity that impacts the test region from different angles is as homogeneous or uniform as possible. In this regard, the variation of the light transmissibility or the back-scattering of the diffusive or reflective body can be influenced, in particular, by the density, the size and/or the shape of openings or of the holes, in a manner that is simple in design.

In a concrete implementation not only of the inspection apparatus but also of the inspection method, it is advantageous if the test region is illuminated with multi-directional light or with light that comes from the lighting body at a varying light intensity below 20%, in particular below 15%, over 120°, in particular over at least 130° or even over at least 135°.

Preferably, the spotlight light source is directed at the lighting body, so that more complex beam paths can be avoided. If necessary, however, part of the light proceeding from the spotlight light source can also be emitted directly onto the test region.

It is also advantageous if the spotlight light source is restricted, in terms of its radiation angle, to the expanse of the lighting body, and thereby—depending on the concrete implementation or the selection of the spotlight light source—radiation losses can be minimized or the risk of possible outside light can be reduced to a minimum.

In a concrete implementation, if a brightness value within a defined brightness value range is detected by the optical sensor, a conclusion can be drawn regarding a glossy region in the test region or in the surface appearance of the test specimen that is situated in the test region. Preferably, the brightness value range is previously established on the basis of the expected surface appearance of the flat items to be tested, because the maximal brightness values that are detected by the camera are not necessarily found in a glossy region. The uniformity of the illumination leads to the result, particularly in the case of reflective regions, that these reflective regions cannot be detected by the optical sensor in excessively overmodulated manner. A glossy region, however, can be defined in a manner so that it can be distinguished from other regions of the surface appearance of a test specimen, by means of a suitable selection of the brightness value range in comparison with brightness values of the remaining surface appearance of the flat items to be inspected, if necessary while taking into consideration other properties of the light detected by the optical sensor, such as, for example, its wavelength or its polarity.

Preferably, the test region is illuminated with multi-directional light, in particular with a varying light intensity below 20%, in particular below 15%, over 120°, in particular over at least 130° or even over at least 135°, and this multi-directional light specifically reduces overmodulation with regard to the brightness values that are measured by the optical sensor to a minimum. This reduction then also brings about correspondingly homogeneous illumination of the test region.

Accordingly, it is advantageous if the lighting body is configured to be correspondingly homogeneous and if variations of the degree of reflection or of the light transmissibility are selected to be as slight as possible, and, if necessary, are adapted solely to the non-homogeneities of the spotlight light source or of the spotlight light sources. Also, variations in the degree of reflection or of the light transmissibility below 20%, in particular below 15%, at over 120°, in particular over at least 130° or even over at least 135°, appear to be advantageous. In this regard, averages should be formed over multiple openings or holes as a function of a hole density or opening density. In particular, it is understood that the homogeneities mentioned above should also be maintained in the region of the beam path from the test region to the sensor or also in the region of other beam paths through the lighting body, in order to guarantee uniform illumination of the test region by the light that proceeds from the lighting body or from the spotlight light sources that spotlight the lighting body, also in the region of these beam paths.

Preferably, the lighting body extends at least in a region having an elliptical cross-section, wherein one focus of the elliptical cross-section lies in the test region and the other focus of the elliptical cross-section lies in the spotlight light source. This arrangement makes it possible, in structurally simple manner, to achieve the most uniform possible illumination of the test region.

In particular, the most uniform possible illumination can be guaranteed if the inspection apparatus has at least two spotlight light sources and if the lighting body extends at least in two regions, each having an elliptical cross-section, wherein one focus, in each instance, of each of the two elliptical cross-sections lies in the test region, and the other focus, in each instance, of each of the elliptical cross-sections lies in one of the two spotlight light sources.

In particular, the two foci that lie in the test region can lie at a common point or, in the case of a linear configuration of the inspection apparatus, can lie on a line.

In this regard, it is conceivable that the camera is disposed precisely in the plane of symmetry or axis of symmetry between the elliptical cross-sections. Likewise, a deviation can be selected here, if this deviation appears to be practical in terms of design, without the method of functioning of the inspection apparatus or the process sequence of the inspection method being lastingly impaired. Preferably, the deviation amounts to less than 45°, in particular less than 30°.

Particularly due to the variation, as already mentioned, of the degree of reflection or of the light transmissibility or of the reflection over the expanse of the lighting body, possible transition regions, in particular, which can be found between the two elliptical cross-sections, can also be adapted to the optical properties of the rest of the lighting body, in terms of their optical properties.

Depending on the concrete implementation, production of a lighting body having an elliptical cross-section can prove to be relatively complex, and this complexity holds true, in particular, for small series, because it is very difficult to form corresponding mirrors or corresponding diffusive or reflective bodies elliptically, in reliable manner, in terms of design. Accordingly, it is advantageous if the lighting body is carried by a corresponding support, which imparts an elliptical shape to the lighting body. It proves to be significantly simpler, in terms of design, if a purely mechanical component has to be brought into a specific shape and this mechanical component, namely the support, then imparts the final shape to the lighting body. Depending on the concrete embodiment of the lighting body, for example if this body comprises a foil or a thin metal sheet, the support does not have to stand in continuous contact with the lighting body, because the inherent rigidity of the lighting body contributes to a sufficiently precise final shape of the lighting body, at least over short distances.

For example, the lighting body can be clamped to the support, so that the corresponding clamping forces also contribute to shaping of the lighting body.

It is understood that the support can particularly have recesses or interruptions where required modules, such as lamps or other light sources and/or the optical sensor, are supposed to be disposed or require a free beam path through the lighting body.

As has already been explained, the relatively uniform illumination of the test region by the lighting body brings about the result that possible surface structures can no longer be detected, or can be detected only with great difficulty or hardly at all. Conversely, as a result, although the surface appearance of embossed regions or also of glossy regions can be inspected in this way, specific other tests lead only to insufficient or deficient results, but these results have to be accepted, for the time being, in order to ultimately permit inspection. In this regard, it proves to be extremely difficult to perform an inspection for edges, in other words for structures brought about by means of embossing, or an inspection for surface defects such as scoring or scratches, using the inspection method and inspection apparatuses described above.

Thus, an inspection of reflective or embossed regions on flat items can be made possible by means of an inspection apparatus for inspection of the surface appearance of a flat item that represents a test specimen, which apparatus comprises at least one direct light source directed at a test region, as well as at least one optical sensor directed at the test region, if the direct light source is directed at the test region by way of a side mirror oriented parallel to a machine direction with one component, along which direction the test specimen passes through the inspection apparatus, and perpendicular to the surface of the flat items to be tested or inspected. Therefore the direct light is also directed at the test specimen or at the test region from as many angles as possible by way of the side mirror.

In this regard, different mechanisms can be utilized in order to be able to recognize edges, scratches or scoring by means of the direct light source. Thus, for example, an attempt can be made, for example in the direct light in the bright field, to recognize the darkened areas caused by edges or scoring or scratches, but this attempt will generally lead to rather unsatisfactory results in view of the secondary task of also testing reflective regions and the overmodulation resulting from this testing. Dark field measurements, in which although the direct light or the direct light source is directed at the test region, but its reflection from the test region is oriented directly next to the optical sensor, have proven to be significantly more practicable, as have oblique light measurements, both of which are oriented in such a manner that light coming from the direct light sources is emitted in a ubiquitous reflection cone at edges, scratches or scoring, so that then, if the orientation of the direct light source is suitable with reference to the scratch to be determined, in each instance, or with reference to the edge or scoring to be determined, in each instance, a corresponding light flash is brought about in the camera.

In this regard, the side mirror makes it possible to aim direct light sources at the test region from very different angles, so that the greatest possible bandwidth can be determined at edges, scratches or scoring in different directions and at different locations in the test region.

In this regard, scratches or scoring parallel to the machine direction are of particular interest, because corresponding defects must be expected with particular frequency, on the basis of the machine property that the flat item passes through the machine parallel to the machine direction.

Preferably, the direct light source is directed at the test region, if necessary by way of the side mirrors, in such a manner that light is reflected closely next to the optical sensor. This reflected light then leads, as was already mentioned above, to a light flash in the optical sensor, if a corresponding edge or scoring or a corresponding scratch passes through the region on the test region that is illuminated by the direct light source.

In order to be able to recognize as intensive a light flash as possible and, in particular, also the flattest edges, scoring or scratches possible, it is advantageous to provide the direct light source with the smallest possible lighting cone, wherein it is ultimately a question of a cost/benefit ratio, how many direct light sources are used, in order to then illuminate the entire test region to a sufficient extent using corresponding direct light. In this regard, it is advantageous, as such, if as many direct light sources as possible are used, as long as the spatial conditions and the stability of the overall arrangement allow this use.

Limits are set particularly with regard to the spatial conditions, however, so that the direct light sources are preferably all disposed above the test region. Direct light sources can also virtually be disposed to the side of the test region, by way of the side mirrors, with it being understood that direct light sources can certainly be provided on the inspection apparatus over a width that exceeds 10% of the width of the test region, and these sources are nevertheless viewed as being provided sufficiently over the test region.

Preferably, the side mirror or each side mirror is configured to be planar, so that the optical conditions between the direct light sources and the test region do not become too complex, and therefore can be represented in relatively simple manner as direct light sources that act as virtual lateral direct light sources that are disposed above the test region or over the space intended for the test specimens to pass through. This simplicity particularly holds true if a plurality of direct light sources are supposed to be replicated as lateral direct light sources, by way of the side mirror.

In and of itself, it can be assumed that the combination of the spotlight light source with its passive lighting body and the direct light source will lead to overlaps in the lighting, which will impair the measurement results, in each instance. In this regard, it can be advantageous to carry out corresponding measurements one after the other or successively in separate apparatuses, but this course of action is relatively complicated in terms of design.

If, however, the direct light sources and the spotlight light sources emit light that can be separated, something that can be implemented by means of different polarity, wavelength or timing, for example, then the measurements can also be carried out in a common inspection apparatus.

Thus, it is conceivable that light having a specific color, for example, is used for the direct light sources or for the direct light source, wherein here, in particular, infrared light or ultraviolet light can also be used, because ultimately, edges, scratches or scoring are mechanical structures that can be seen in the infrared range or in the ultraviolet range, as well, so that the entire visible range can be used for the spotlight light source, which ultimately is generally supposed to test the optical appearance.

In particular, the light of both the direct light source and the spotlight light source can be detected by way of a common optical sensor, and this arrangement ultimately facilitates an evaluation and, in particular, also the structure of the inspection apparatus. It is understood that alternatively, it is also easily possible, accordingly, to use multiple optical sensors, which can, in particular, be configured differently from one another and suitably optimized for the separable light of the direct light source and the spotlight light source, if applicable, wherein it is understood that multiple optical sensors, for example, can merely be used to detect the light of the spotlight light source, if this appears to be suitable.

In this regard, a first measurement channel can be formed by means of the spotlight light source, while a second measurement channel can be formed by means of the direct light source.

Preferably, edge detection or scratch detection takes place by way of the second measurement channel, in the bright field or the dark field, wherein a brightness ratio can be determined between the first measurement channel and the second measurement channel. If the brightness ratio lies within a defined brightness ratio range, it is possible to conclude that a glossy region exists in the test region or in the surface appearance of the test specimen that is situated in the test region.

This conclusion takes advantage of a glossy region free of scratches or edges in direct lighting appearing darker in the camera image than a comparatively brighter non-glossy region, because the non-glossy region scatters light in all directions. In this manner, particularly in combination with the brightness values of the first measurement channels or with the brightness value brought about by the spotlight light source, it is also possible to distinguish glossy regions from regions that happen to appear equally bright in the indirectly illuminated image but are not glossy, in relatively operationally reliable manner.

As was already explained above, it is advantageous if the inspection apparatus is configured to be essentially consistent or uniform perpendicular to a machine direction. Accordingly, it is advantageous if the lighting body as well as the spotlight light source extend with a consistent cross-section in a transverse direction that is configured transverse to the machine direction. The same also holds true for the optical sensor, insofar as its extent is required over a great width in the transverse direction. In the case of a suitable optical structure, the optical sensor can be selected to be significantly narrower in the transverse direction than the rest of the inspection apparatus and, in particular, than the lighting body or the arrangement of the spotlight light source. Nevertheless, it remains that the optical sensor, the lighting body, and the spotlight light source preferably extend, at least in the transverse direction, over the width of the optical sensor, preferably at a consistent cross-section, in order to fulfill these geometrical conditions in the best possible way, while it is already advantageous, as such, if the lighting body, the spotlight light source, and possibly the optical sensor extend, in the transverse direction, over the width of the test region at a consistent cross-section.

It is understood that the optical sensor can be provided by means of very different camera systems. In particular, linear cameras or matrix cameras can be used here, wherein the matrix cameras can be used for wavelength splitting in the machine direction, if applicable. Accordingly, in practice the optical sensor will be formed from a plurality of sensor elements disposed next to one another at least in the transverse direction. Likewise, in practice, the spotlight light source will frequently comprise a plurality of individual lighting sources, for example a plurality of light-emitting diodes, if it is not formed by means of a fluorescent tube that extends in the transverse direction.

It is understood that the optical sensor can be oriented perpendicular on the test region. As was already indicated above, however, smaller angle deviations are easily conceivable, without the result of the inspection significantly suffering in this regard.

Preferably, the tested flat items are printed materials, such as packaging and the like, for example. In this regard, it is understood that application of the glossy regions or of the embossings can certainly be provided not by printing technology measures but rather, if applicable, also in a different way, such as, for example, by coating or spraying. Furthermore, it is understood that checking of the flat items is not restricted to printed materials, but rather, in particular, can also comprise other planar arrangements, which certainly can have a certain surface structure, such as, for example, credit cards or circuit boards.

It is understood that the characteristics of the solutions described above and in the claims can also be combined, if applicable, in order to be able to implement the advantages cumulatively, accordingly.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings,

FIG. 7 is a schematic section along a machine direction through a fifth inspection apparatus;

FIG. 8 is a schematic section along a machine direction through a sixth inspection apparatus; and FIG. 9 is a schematic section along a machine direction through a seventh inspection apparatus.

DETAILED DESCRIPTION OF PREFERRED EMBODIMENTS

Figure 1:
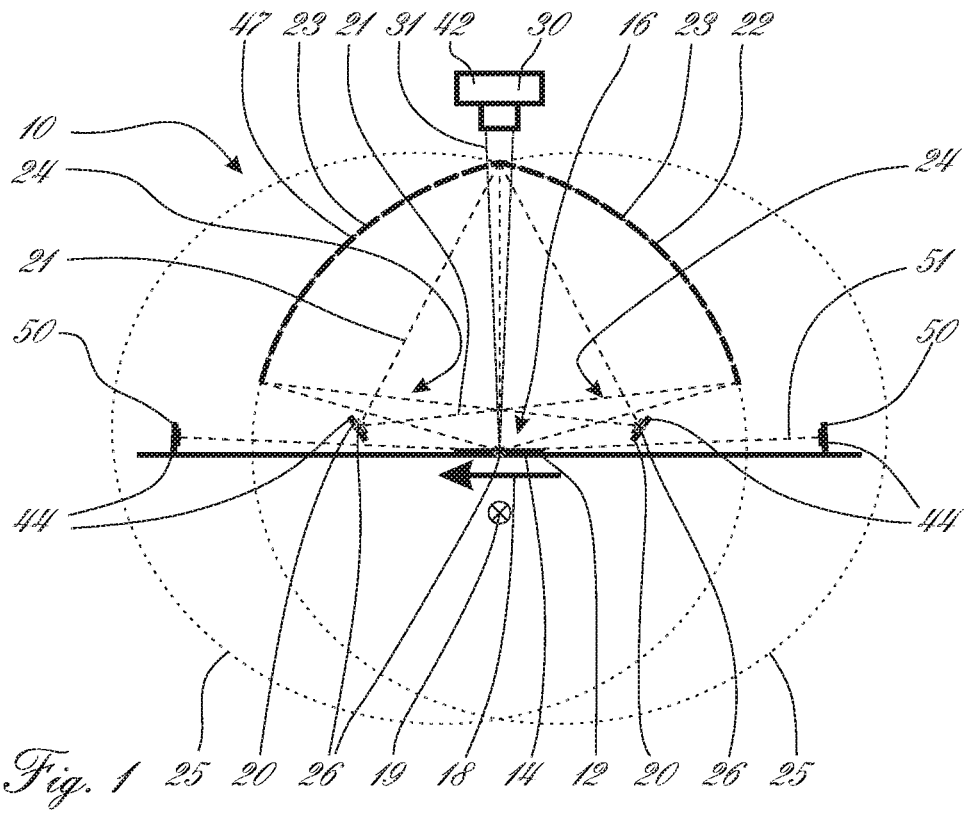
FIG. 1 is a schematic section along a machine direction through a first inspection apparatus.

In each instance, flat items 14 that represent test specimens 12 pass through the inspection apparatuses 10 shown in the figures, along a machine direction 18; the apparatuses have a test region 16, which extends essentially along a transverse direction 19, which is defined perpendicular to the machine direction 18.

Figure 5:
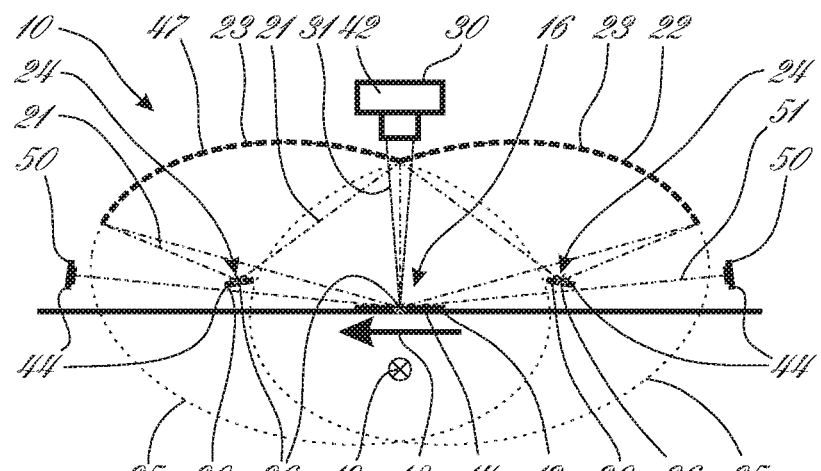
FIG. 5 is a schematic section along a machine direction through a third inspection apparatus.
Figure 6:
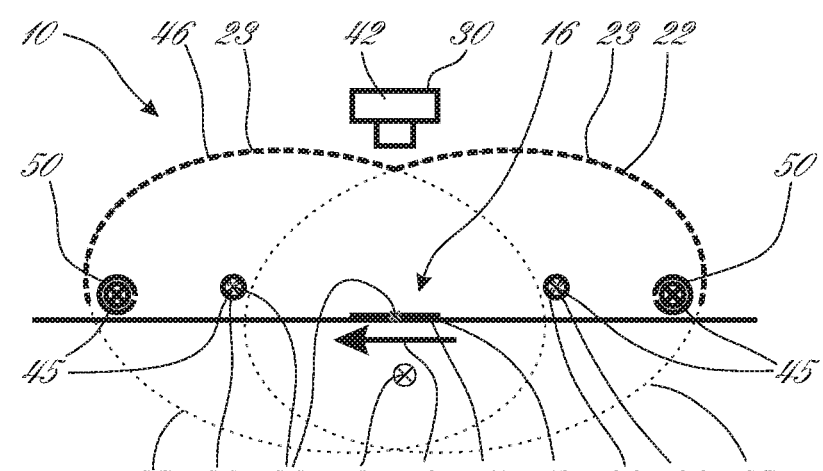
FIG. 6 is a schematic section along a machine direction through a fourth inspection apparatus.

It is understood that the exemplary embodiments shown in FIGS. 1, 5, and 6, which are shown only in cross-section, can also be configured with rotation symmetry or essentially with rotation symmetry, if this configuration appears to be necessary or practical.

The inspection apparatuses each have spotlight light sources 20, which radiate onto a lighting body 22 with their beam path 21, which in turn illuminates the test region 16.

In this regard, the inspection apparatuses shown in FIGS. 1 to 6 each have two regions 23, and the inspection apparatuses shown in FIGS. 7 to 9 each have only one region 23, which extend, in each instance, with an elliptical cross-section 25 (indicated with a dotted line) and, by their nature, each have two foci 26.

In this regard, one of the foci 26 of each region 23, in each instance, lies in the test region 16, while a spotlight light source 20 can be found in the respective other focus 26. In the exemplary embodiments according to FIGS. 1 to 6, the foci 26 each lie at a point or on a line, which point or line is then uniformly illuminated, accordingly.

In the exemplary embodiments of FIGS. 1 to 5, LED strips 44 are used as spotlight light sources 20, in each instance, while in the exemplary embodiments according to FIGS. 6 to 9, fluorescent tubes 45 are used in this regard.

The fluorescent tubes 45 of the exemplary embodiments according to FIGS. 7 to 9 are partially covered, so that these tubes, just like the LED strips 44 of the exemplary embodiments according to FIGS. 1 to 5, radiate onto the lighting body 22 at a beam angle 24 that is directed at and restricted to the related region 23 having an elliptical cross-section 25, in each instance. In the exemplary embodiment according to FIG. 6, this arrangement does not appear to be necessary in concrete terms, because here, too, light coming in the direction from the spotlight light source is used for uniform illumination of the test region 16, but if applicable, this light can also be dispensed with, if such dispensing with contributes to the homogeneity of the light emission.

As is directly evident, the lighting body 22, in all the exemplary embodiments, extends continuously over at least 135° in the drawing plane, which represents the cross-section, which plane represents a cross-section plane, in each instance, oriented perpendicular on the surface of the flat items 14 to be tested or inspected, and parallel to the machine direction 18 or perpendicular to the transverse direction 19. Nevertheless, it is understood that in deviating exemplary embodiment, an expanse over smaller angles, in particular, for example, 120° or even less, is also conceivable, if this arrangement appears sufficient for the present inspection task, and this expanse over smaller angles holds true, in particular, if the lighting body 22 is configured to be partially transmissible, as is the case for the inspection apparatuses 10 according to FIGS. 1 to 8. Because an optical sensor 30 can be directed through the lighting body, which is configured to be partially transmissible, onto the test region 16 in these embodiments, as is the case for the exemplary embodiments according to FIGS. 1 to 8, very great homogeneity occurs directly, even in the region that lies in the direct viewing field of the optical sensor 30, which region is of the most interest.

Figure 2:
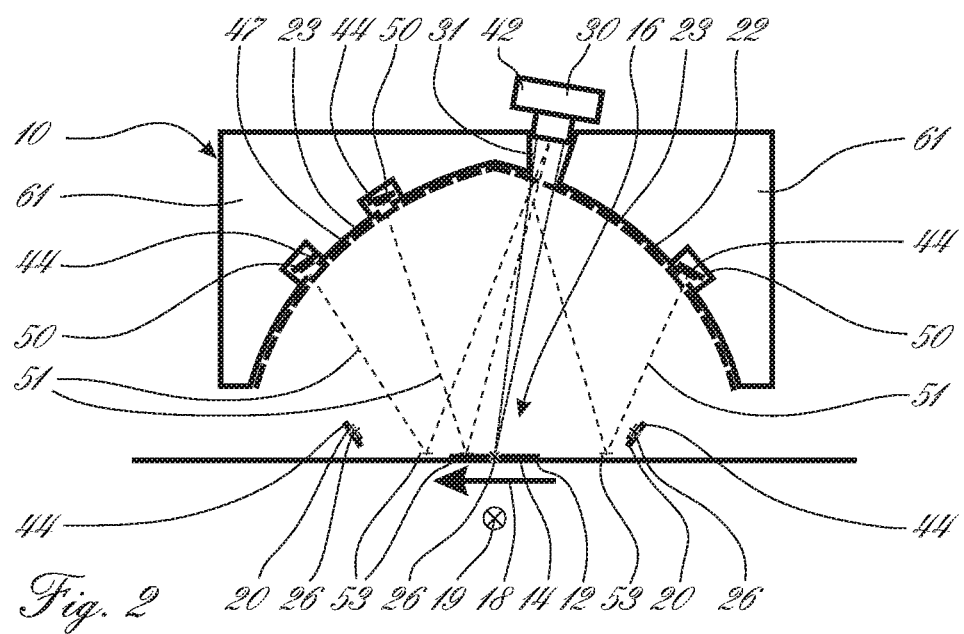
FIG. 2 is a schematic section along a machine direction through a second inspection apparatus.

In this regard, the viewing field of the optical sensor 30 is essentially defined by an optical beam path 31, as shown as an example in FIGS. 1, 2, and 5, and is also directed at the foci 26 that lie in the test region 16.

In the exemplary embodiments shown in FIGS. 8 and 9, the optical sensor 30 does not look through the lighting body 22, wherein for reasons of space a mirror 32 is disposed in the beam path 31 of the optical sensor 30 of the inspection apparatus 10 according to FIG. 9, on the basis of which the optical sensor 30 can be directed past the lighting body 22 on the test region 16. Such an arrangement has a correspondingly shorter construction in the machine direction 18.

In all the exemplary embodiments, not only the spotlight light sources 20 and the related optical or other measures, but also at least one direct light source 50 is provided, in each instance, which is directed at the test region 16 directly or by way of a planar side mirror 52. Such a side mirror 52 is shown as an example in FIGS. 3 and 4. In deviating embodiments, the side mirror 52 can also be configured not to be planar although this configuration might lead to extremely complex optical images of the direct light sources 50, if applicable, this complexity might then be intentionally wanted or be accepted.

The direct light sources 50 radiate a comparatively defined beam path 51 into the test region 16 and serve to recognize edges, scratches or scoring or other three-dimensional structures, which as such are very difficult to identify by means of the all-around lighting or by the lighting over a very large angle range, based on the spotlight light sources 20 and the related lighting bodies 22.

For this purpose, the spotlight light sources 20 form a first measurement channel and the direct light sources 50 form a second measurement channel, wherein in all the exemplary embodiments, the light sources 20, 50 of the two measurement channels differ in terms of their wavelength. In this manner, it is possible to carry out both measurements at the same time and, if necessary, also using the same optical sensor 30, as shown as an example using the exemplary embodiments of FIGS. 1 to 7 and 9. It is understood that in deviating exemplary embodiments, as shown as an example in FIG. 8, for example, a separate optical sensor 30 can also be used in this regard.

In deviating embodiments, the light of the direct light sources 50 and of the spotlight light sources 20 can also be selected so that it can be separated in another way, for example on the basis of its polarity or timing. It is understood that in deviating embodiments, separate measurements can also be undertaken or it is possible to dispense with a measurement by means of the direct light sources 50 entirely.

The second measurement channel is implemented, in the exemplary embodiments according to FIGS. 1, 5 to 7, and 9, by means of the direct light sources 50, which emit a sidelight, so that the direct light source 50 of these exemplary embodiments is directed at the focus of the optical sensor 30.

This result is different in the case of the exemplary embodiments according to FIGS. 2 to 4 and 8, which carry out measurements in the dark field, so that the direct light sources are directed at the test region 16 in an impact region 53 (see FIGS. 2 and 4 as examples), which is reflected directly next to the optical sensor 30. As a result, a changed reflection direction, as it is caused by edges, scratches or scoring, then leads to a reflection into the optical sensor 30, so that a corresponding signal can be detected by or output by the optical sensor 30.

Figure 3:
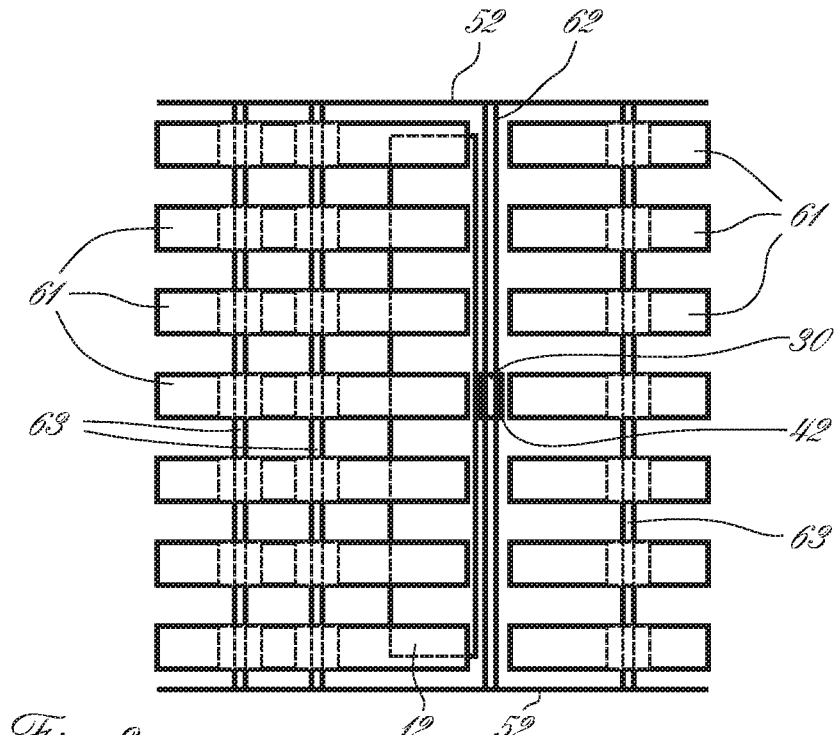
FIG. 3 is a schematic top view of the inspection apparatus according to FIG. 2.
Figure 4:
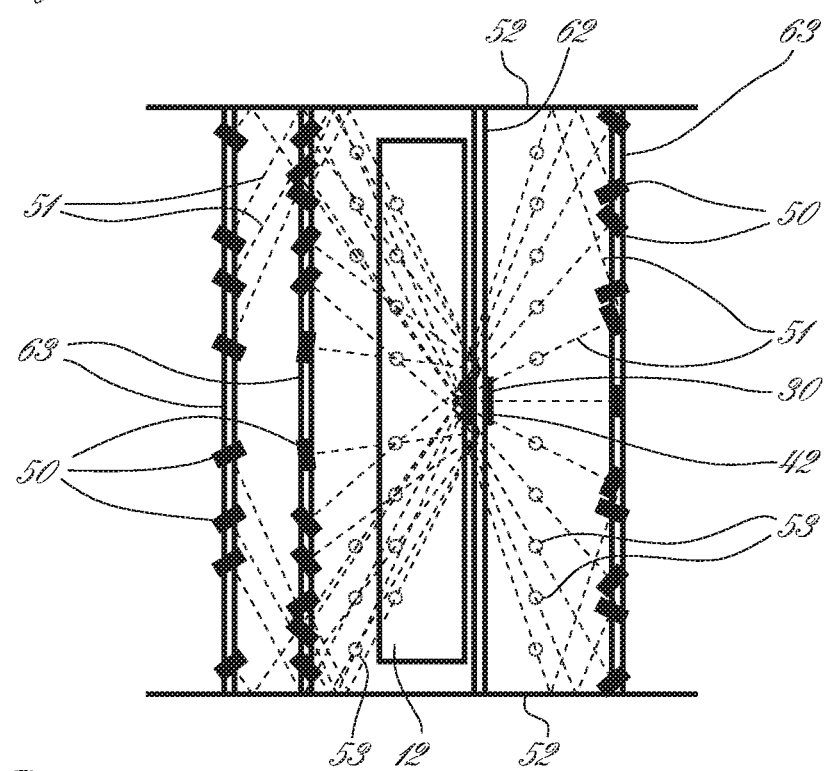
FIG. 4 shows schematically, the placement of direct light sources of the inspection apparatus according to FIGS. 2 and 3 in a representation similar to FIG. 3.

In the present inspection apparatuses 10, the optical sensor 30 is configured as a line camera 42, in each instance, wherein the line camera 42—depending on the concrete selection—extends over only part of the width of the respective inspection apparatus 10 in the transverse direction 19, as shown as an example in FIGS. 3 and 4. In this regard, optics known as such from the state of the art ensure that the entire test region 16 and, in particular, the width of the inspection apparatus 10 that extends in the transverse direction 19, through which width the test specimens 12 or flat items 14 run are detected by the line camera 42. Depending on the concrete selection, the line camera can also have a greater width. In alternative embodiments, a matrix camera can also be used instead of the line camera, wherein—if applicable—the sensor elements of the matrix camera, which are disposed one behind the other in the machine direction 18, can be used for spectral analysis or for checking or measuring different measurement channels.

In the exemplary embodiments according to FIGS. 1 to 5, LED strips 44 are used both as spotlight light sources 20 and as direct light sources 50, in each instance, wherein the individual LEDs of the LED strips 44 of the direct light sources are oriented differently, as is shown as an example in FIG. 4. In this manner, the beam paths 51 of the direct light sources 50 can be oriented individually, in suitable manner, with reference to the optical sensor 30.

In order to guarantee a suitable position, both line camera 42 and also the direct light sources 50 are disposed on suitable supports 62, 63. The same holds true also for the spotlight light sources 20, although the related supports are not explicitly shown in the figures, because these sources are merely conventional LED strips 44.

In the exemplary embodiments according to FIGS. 6 to 9, fluorescent tubes 45 are used both as spotlight light sources 20 and also as direct light sources 50; these sources are shielded, if necessary, in order to suitably limit the beam path 21, 51. Depending on the concrete implementation of these exemplary embodiments, here, too, further optical devices, such as linear lenses or the like, for example, can be used.

It is understood that in deviating embodiments, the light sources 20, 50 of the inspection apparatuses 10 according to FIGS. 6 to 9, can also be implemented by means of LEDs, if necessary this implementation also applies for individual light sources. Likewise, it is conceivable to constitute the LED strips 44 of the exemplary embodiments according to FIGS. 1 to 5 by means of fluorescent tubes, if this arrangement appears advisable or practical for deviating exemplary embodiments.

The lighting body 22 of the exemplary embodiments according to FIGS. 1 to 4 is configured as a reflective body 47 having holes, thereby making a partially transmissible lighting body 22 available. In this regard, the density of the holes of these reflective bodies 47 as well as the foci of the optical sensor 30 and of the direct light sources 50 are selected in such a manner that the reflective body 47 impairs the corresponding beam paths 31, 51 only insignificantly.

As shown as an example using the inspection apparatus 10 according to FIGS. 2 to 4, the reflective body 47 can be carried by supports 61, which impart the shape to the reflective body 47 or the lighting body 22, in that these bodies 22, 47 are clamped in the respective supports 61, so that the respective body needs to demonstrate its final shape only approximately, before it is clamped into the supports 61. The tension caused by this clamping and also the inherent rigidity then bring about the result that the reflective body 47 or the lighting body 22 assumes the basic shape predetermined by the supports 61 also in regions of non-numbered recesses for the optical sensor 30, the direct light sources 50, and other modules. It is understood that in deviating embodiments, in particular also in the case of the inspection apparatus 10 according to FIG. 1, inherently rigid lighting bodies 22 can be used.

A reflective body 47 having holes is also used in the inspection apparatus 10 according to FIG. 5; by its nature, its basic shape deviates slightly from the basic shape of the reflective body 47 or the lighting body 22 of the inspection apparatus 10. It is understood that here, too, a self-supporting lighting body 22 or reflective body 47 or, alternatively, a lighting body 22 or reflective body 47 carried by supports can be used.

In the inspection apparatuses 10 shown in FIGS. 6 and 8, a diffusive body 48 having holes is used as a lighting body 22, in each instance. Such a diffusive body is provided with an opaque surface that emits light diffusely, as uniformly as possible, instead of with a surface that is mirrored in the direction of the test region 16, wherein the holes of this diffusive body 48, similar to the holes of the reflective bodies 47, serve to make the respective lighting body 22 partially transmissible.

It is understood that in the exemplary embodiments according to FIGS. 6 and 8, reflective bodies 47 can also be used instead of the diffusive bodies 48, and that in the exemplary embodiments according to FIGS. 1 to 5, diffusive bodies 48 can also be used instead of the reflective bodies 47, if this use appears advantageous. Depending on the concrete implementation, the diffusive bodies 48 can be configured to be self-supporting or inherently rigid, which is generally easier than in the case of reflective bodies 47. It is understood that the diffusive bodies 48 can also be given their shape by way of supports in specific concrete implementation forms.

In the inspection apparatus 10 according to FIG. 7, a semi-transmissible mirror 46 is used instead of the reflective or diffusive bodies 47, 48, wherein it is understood that here, too, reflective bodies 47 or diffusive bodies 48, each having holes, can be used instead of the semi-transmissible mirror 46. Likewise, it is conceivable semi-transmissible mirrors 46 are used also in the case of the exemplary embodiments according to FIGS. 1 to 6 and 8. Also, the semi-transmissible mirror 46 can preferably be configured to be inherently rigid. Likewise, it is conceivable that this semi-transmissible mirror 46 is given its shape by way of separate or external supports in deviating embodiments.

In the inspection apparatus 10 according to FIG. 9, a lighting body 22 configured to be semi-transmissible was dispensed with and instead, a diffusive body 49 is used as a lighting body 22. Because of the lack of light transmissibility or due to the non-transmissibility of the lighting body 22 of the inspection apparatus 10 according to FIG. 9, the optical sensor 30 of this exemplary embodiment looks past the lighting body 22, with a mirror 32 being provided for this purpose, to minimize the spatial expanse in the machine direction 18, by way of which mirror the optical sensor 30 looks into the test region 16. In deviation, it is conceivable that the optical sensor 30 looks directly into the test region 16, as this arrangement is shown as an example in the exemplary embodiment according to FIG. 8; in the case of this inspection apparatus 10, the direct light source 50 and a related optical sensor 30 radiate light at and detect the test region 16, respectively, through the lighting body 22 of the inspection apparatus 10 according to FIG. 8; in this exemplary embodiment, this detection takes place by means of a dark field measurement, in that the direct light source 50 of the inspection apparatus 10 according to FIG. 8 is directed at an impact region (not numbered separately in FIG. 8), by which the light of the direct light source 50 is reflected slightly in front of or slightly behind the related optical sensor 30, in the machine direction 18.

Although the inspection apparatus 10 according to FIG. 8 uses separate optical sensors 30 or line cameras 42 for measuring the light emitted by the spotlight light source 20, on the one hand, and by the direct light source 50, on the other hand, this measuring is done, in the exemplary embodiments according to FIGS. 1 to 7 and 9, in each instance, by means of the same optical sensor 30 or by means of the same line camera 42.

In the exemplary embodiments of FIGS. 1 to 8, the distribution of the holes varies, wherein in deviating embodiments, other openings such as slots or the like can also be used instead of the holes, or the mirroring over the expanse of the lighting body 22 in the machine direction 18, so that the light of the spotlight light sources 20 reaches the test region 16 as homogeneously as possible. In this regard, the homogeneity is selected in such a manner that the light intensity varies below 20%, preferably below 15%, over 135°.

The diffusive bodies 48, 49 furthermore bring about the result that the test region 16 is illuminated with multi-directional light.

As is directly comprehensible, the inspection apparatuses 10 according to FIGS. 1 and 5 have a significantly narrower construction in the machine direction 18 than the inspection apparatuses 10 according to FIGS. 5 and 6; this difference results from selecting the elliptical cross-sections 25 with a significantly greater overlap and from having the respective focus 26, in which the spotlight light source 20 can be found, lie closer to the region 23 of the lighting body 22, which is irradiated by the respective other spotlight light source 20.

In the exemplary embodiment according to FIGS. 1 and 5, the direct light sources 50 are situated outside of the space surrounded by the lighting bodies 22, while this placement is not the case for the exemplary embodiments according to FIGS. 2 and 6.

In particular, the direct light sources 50 of the inspection apparatuses 10 according to FIGS. 1 and 5 to 7 as well as FIG. 9 do not need to radiate through the respective lighting bodies 22, as is the case for the exemplary embodiments according to FIGS. 2 to 4 and 8. In the case of a suitable selection of the holes or of the transparency of the semi-transmissible mirror, this radiation proves to be somewhat non-critical.

As is directly evident using FIGS. 3 and 4, it is possible, particularly on the basis of the side mirrors 52, to dispose all the direct light sources on a width that exceeds the width of the test region 16 by less than 10%.

Although only a few embodiments of the present invention have been shown and described, it is to be understood that many changes and modifications may be made thereunto without departing from the spirit and scope of the invention.

What is claimed is:

1. An inspection apparatus for inspection of a surface appearance of a flat item representing a test specimen, the inspection apparatus comprising:
   (a) a spotlight light source;
   (b) a partially transmissible passive lighting body spotlighted by the spotlight light source and illuminating a test region; and
   (c) at least one optical sensor directed at the test region and disposed with reference to the test region, optically beyond the passive lighting body and detecting the test region through the passive lighting body;
   wherein the spotlight light source is directed at the passive lighting body and the passive lighting body extends continuously over at least 120° in a section plane perpendicular to a surface of the flat item to be inspected.

2. An inspection apparatus for inspection of a surface appearance of a flat item representing a test specimen, the inspection apparatus comprising:
   (a) a spotlight light source;
   (b) a passive lighting body spotlighted by the spotlight light source and illuminating a test region; and
   (c) at least one optical sensor directed at the test region;
   wherein the spotlight light source is directed at the passive lighting body and the passive lighting body extends continuously over at least 120° in a section plane perpendicular to a surface of the flat item to be inspected.

3. The inspection apparatus according to claim 1, wherein the passive lighting body is at least one of a semi-transmissible mirror and a light-transmissible diffusive or reflective body.

4. The inspection apparatus according to claim 3, wherein the diffusive or reflective body has holes.

5. The inspection apparatus according to claim 3, wherein the diffusive or reflective body has a degree of reflection or a light transmissibility varying over an expanse of the passive lighting body.

6. The inspection apparatus according to claim 4, wherein the holes are distributed over an expanse of the passive lighting body in varying density.

7. The inspection apparatus according to claim 1, wherein the spotlight light source is directed at the passive lighting body or is restricted to an expanse of the lighting body in terms of a beam angle of the spotlight light source.

8. An inspection apparatus for inspection of a surface appearance of a flat item representing a test specimen, the inspection apparatus comprising:
   (a) a spotlight light source;
   (b) a partially transmissible passive lighting body spotlighted by the spotlight light source and illuminating a test region; and
   (c) at least one optical sensor directed at the test region and disposed with reference to the test region, optically beyond the passive lighting body and detecting the test region through the passive lighting body;
   wherein the lighting body extends at least in a region having an elliptical cross-section with a first focus and a second focus, and wherein the first focus of the elliptical cross-section lies in the test region, and the second focus of the elliptical cross-section lies in the spotlight light source.

9. The inspection apparatus according to claim 1, further comprising a direct light source, wherein the direct light source and the spotlight light source emit light that can be separated, on the basis of at least one of polarity, wavelength and timing, or wherein the light emitted by the direct light source and the spotlight light source is detected by way of a common optical sensor, or the light of the direct light source and the light of the spotlight light source is detected by way of at least two optical sensors that are different from one another.

10. An inspection method for inspection of a surface appearance of a flat item representing a test specimen, the inspection method comprising:
    (a) indirectly illuminating a test region by way of a passive lighting body spotlighted by a spotlight light source; and
    (b) detecting by way of at least one optical sensor light proceeding from the test region;
    wherein the optical sensor detects the test region through the lighting region; or
    wherein the test region is continuously illuminated over at least 120° in a section plane perpendicular to a surface of the flat item to be inspected.

11. The inspection method according to claim 10, wherein the optical sensor detects a brightness value within a defined brightness value range when a glossy region exists in the test region or in the surface appearance of the test specimen situated in the test region (16).

12. The inspection method according to claim 10, wherein the test region is illuminated with multi-directional light.

13. The inspection method according to claim 12, wherein the multi-directional light has a light intensity varying over 120° and below 20%.

14. The inspection method according to claim 13, wherein the light intensity varies over 135° and below 15%.

15. The inspection method according to claim 10, wherein a first measurement channel is formed by the spotlight light source, and edge detection or scratch detection takes place by way of a second measurement channel, or wherein a brightness ratio is determined between a first measurement channel and a second measurement channel, wherein the brightness ratio indicates that a glossy region exists in the test region or in the surface appearance of the test specimen that is situated in the test region when the brightness ratio lies within a defined brightness ratio range.

16. The inspection apparatus according to claim 2, wherein the section plane has the optical sensor and a beam path of the optical sensor or wherein the section plane is oriented parallel to a machine direction or perpendicular to a transverse direction.

17. The inspection apparatus according to claim 1, wherein at least one of the passive lighting body and the spotlight light source extends in a transverse direction at a uniform cross-section.

18. The inspection apparatus according to claim 1, wherein the flat item is printed material.

19. The inspection apparatus according to claim 8, wherein the inspection apparatus has at least a first spotlight light source and a second spotlight light source, and the passive lighting body extends in at least first and second regions, the first region having a first elliptical cross-section with a first focus and a second focus and the second region having a second elliptical cross-section with a third focus and a fourth focus, wherein the first and third foci lie in the test region and the second and fourth foci lies in one of the first and second spotlight light sources.

20. The inspection apparatus according to claim 2, wherein the passive lighting body is at least one of a semi-transmissible mirror and a light-transmissible diffusive or reflective body.

21. The inspection apparatus according to claim 20, wherein the diffusive or reflective body has holes.

22. The inspection apparatus according to claim 20, wherein the diffusive or reflective body has a degree of reflection or a light transmissibility varying over an expanse of the passive lighting body.

23. The inspection apparatus according to claim 21, wherein the holes are distributed over an expanse of the passive lighting body in varying density.

24. The inspection apparatus according to claim 2, wherein the spotlight light source is directed at the passive lighting body or is restricted to an expanse of the lighting body in terms of a beam angle of the spotlight light source.

25. The inspection apparatus according to claim 2, wherein the lighting body extends at least in a region having an elliptical cross-section with a first focus and a second focus, and wherein the first focus of the elliptical cross-section lies in the test region, and the second focus of the elliptical cross-section lies in the spotlight light source.

26. The inspection apparatus according to claim 25, wherein the inspection apparatus has at least a first spotlight light source and a second spotlight light source, and the passive lighting body extends in at least first and second regions, the first region having a first elliptical cross-section with a first focus and a second focus and the second region having a second elliptical cross-section with a third focus and a fourth focus, wherein the first and third foci lie in the test region and the second and fourth foci lies in one of the first and second spotlight light sources.

* * * * *